United States Patent [19]

Kordes

[11] Patent Number: Plant 7,510

[45] Date of Patent: Apr. 30, 1991

[54] ROSE PLANT KORXENNA

[75] Inventor: Wilhelm Kordes, Sparrieshoop, Fed. Rep. of Germany

[73] Assignee: Bear Creek Gardens, Inc., Medford, Oreg.

[21] Appl. No.: 475,976

[22] Filed: Feb. 6, 1990

[51] Int. Cl.[5] ..... A01H 5/00

[52] U.S. Cl. ..... Plt./21

[58] Field of Search ..... Plt./21

*Primary Examiner*—James R. Feyrer

*Attorney, Agent, or Firm*—Klarquist, Sparkman, Campbell, Leigh & Whinston

[57] ABSTRACT

A hybrid tea rose variety having large high centered red flowers, good yield of long stemmed greenhouse cut roses (160 stems/m$^2$), disease resistant foilage, and five (5) to seven (7) leaflet leaves.

1 Drawing Sheet

This present invention relates to a new and distinct variety of rose plant named Korxenna of the hybrid tea class which was originated by me by crossing the variety Allegro with the variety Dallas.

The primary objective of this breeding was to produce a new rose variety having bright red hybrid tea flowers, long stems, high yield for greenhouse cut flower production, disease resistant foliage and good vase life. The objective was substantially achieved long with other desirable improvements as evidenced by the following unique combination of characteristics which are outstanding in the new variety and which distinguish it from its parents as well as from all other varieties of which I am aware:

1. Large high centered red flowers.
2. Good yield of long stemmed greenhouse cut roses (160 stems/m$^2$).
3. Disease resistant foliage.
4. Five (5) to seven (7) leaflet leaves.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Allegro.

*Pollen parent.*—Dallas.

Classification:

*Botanical.*—*Rosa hybrida.*

*Commercial.*—Hybrid tea.

FLOWER

Observations made from specimens grown in a greenhouse environment in Somis, Calif.

Blooming habit: Recurrent.

Bud:

*Size.*—1¾ inch when the petals start to unfurl.

*Form.*—Long, pointed ovoid.

*Color.*—When sepals first divide: Red Group 46A. When half blown: The upper sides of the petals are Red Group 44A; and the lower sides of the petals are Red Group 44A.

*Sepals.*—Color: Green Group 138B. Surface texture: Covered in fine hairs. Three normally appendaged sepals and two unappendaged sepals with hairy edges.

*Receptacle.*—Color: Medium green. Shape: Funnel. Size: Medium. Surface: Smooth.

*Peduncle.*—Length: Medium. Surface: Smooth. Color: Mediumg green. Strength: Stiff, erect.

Bloom:

*Size.*—Large. Average open size is 4 to 4½ inches.

*Borne.*—Singly.

*Stems.*—Long, strong.

*Form.*—When first open: High centered. Permanence: Retains its form to the end, outer petal edges curl slightly.

*Petalage.*—Number of petals under normal conditions: 35.

*Color.*—Upper side of petals is: Red Group 44A. Reverse side of petals is: Red Group 44A. Base of petals is: A very small yellowish white half moon at the point of attachment. Major color on the upper side is: Red Group 44A.

*Variegations.*—Occasional white streak on the outer petals.

*Discoloration.*—General tonality at end of first day: No change; at the end of the third day: No change.

*Fragrance.*—Slight.

Petals:

*Texture.*—Thick.

*Shape.*—Round, notched.

*Form.*—Tips slightly recurved.

*Arrangement.*—Imbricated. Petaloids in the center: Few.

*Persistence.*—Drop off cleanly.

*Lastingness.*—On the plant: Very long. As a cut flower: Very long.

Reproductive parts:

*Anthers.*—Size: Large. Quantity: Many. Color: Reddish brown. Arrangement: Regular around styles.

*Filaments.*—Color: Yellow.

*Pollen.*—Color: Gold yellow.

*Styles.*—Color: Red.

*Stigmas.*—Color: Greenish white.

Form: Bush.

Growth: Very vigorous, upright.

Foliage:

*Number of leaflets on normal mid-stem leaves.*—5 to 7.

*Size.*—Large.

*Quantity.*—Normal.

*Color.*—New foliage: Reddish. Old foliage: Dark green.

Leaflets:

*Shape.*—Oval to pointed oval.

*Texture.*—Leathery.

*Edge.*—Serrated.

*Serration.*—Single, small.

*Petiole.*—Rachis: Reddish. Underside: Smooth with some prickles.

*Stipules.*—Medium, bearded.

*Disease resistance.*—Resistant to powdery mildew under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked downward.

*Color when young.*—Red.

Small prickles:

*Quantity.*—On main stalks: None. On laterals: None.

*Color.*—Green.

I claim:

1. A new and distinct variety of rose plant of the hybrid tea class, substantially as herein shown and described, characterized particularly as to novelty by its strong disesase resistant foliage, long stems, high yield of cut stems, large bright red flowers and five (5) to seven (7) leaflet leaves.

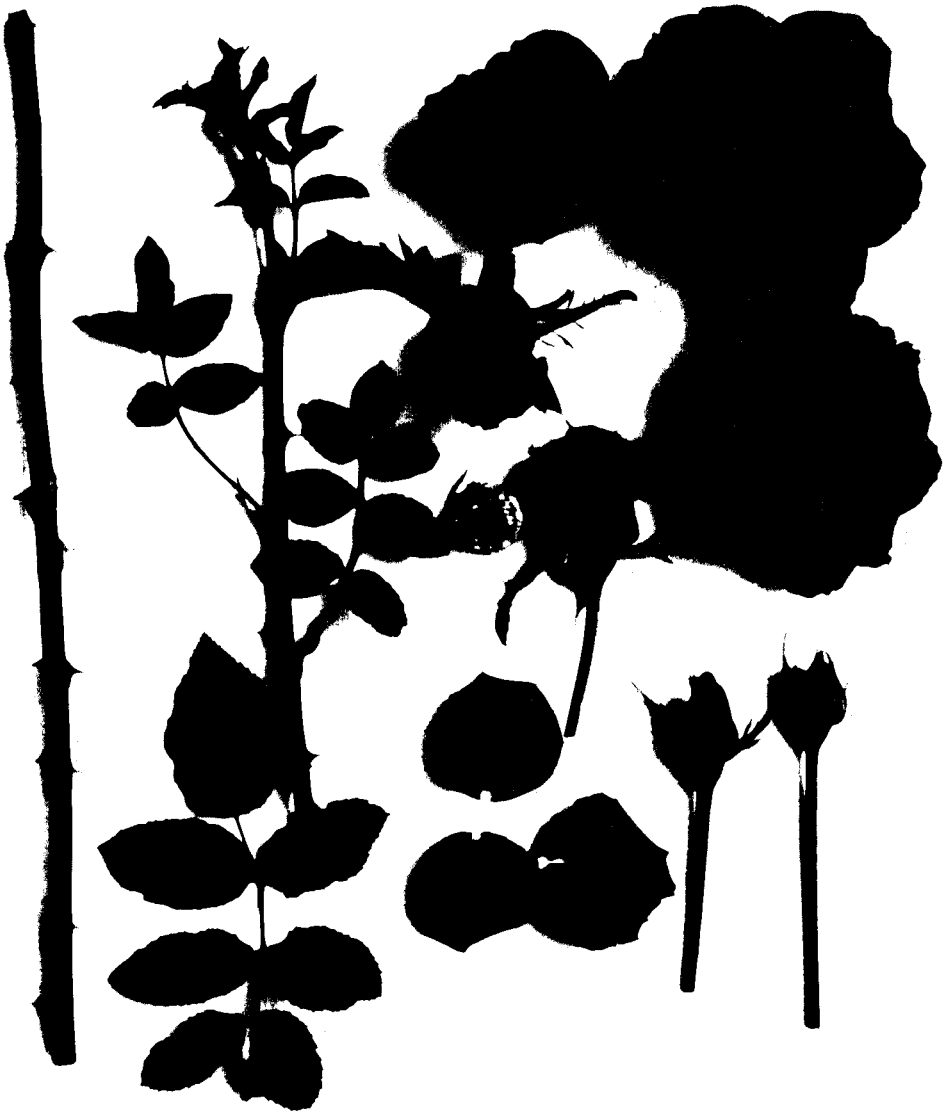

* * * * *